(12) United States Patent
Elmaleh

(10) Patent No.: US 10,532,104 B2
(45) Date of Patent: Jan. 14, 2020

(54) BIOTIN COMPLEXES FOR TREATMENT AND DIAGNOSIS OF ALZHEIMER'S DISEASE

(71) Applicant: The General Hospital Corporation, Boston, MA (US)

(72) Inventor: David R. Elmaleh, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/601,170

(22) Filed: May 22, 2017

(65) Prior Publication Data

US 2017/0326244 A1 Nov. 16, 2017

Related U.S. Application Data

(62) Division of application No. 14/421,022, filed as application No. PCT/US2013/057566 on Aug. 30, 2013, now Pat. No. 9,655,977.

(60) Provisional application No. 61/695,487, filed on Aug. 31, 2012.

(51) Int. Cl.
| | |
|---|---|
| A61K 47/55 | (2017.01) |
| C12N 15/113 | (2010.01) |
| A61K 31/4188 | (2006.01) |
| A61K 31/713 | (2006.01) |
| C12N 15/11 | (2006.01) |
| A61K 49/08 | (2006.01) |
| A61K 51/04 | (2006.01) |
| A61K 47/54 | (2017.01) |

(52) U.S. Cl.
CPC ........ *A61K 47/551* (2017.08); *A61K 31/4188* (2013.01); *A61K 31/713* (2013.01); *A61K 47/549* (2017.08); *A61K 49/085* (2013.01); *A61K 51/0497* (2013.01); *C12N 15/111* (2013.01); *C12N 15/113* (2013.01); *C12N 2310/14* (2013.01); *C12N 2310/3517* (2013.01)

(58) Field of Classification Search
CPC .............. A61K 47/549; A61K 31/4188; A61K 31/713; C12N 15/111; C12N 15/113
See application file for complete search history.

(56) References Cited

U.S. PATENT DOCUMENTS

| | | | |
|---|---|---|---|
| 3,420,788 A | 1/1969 | Solms | |
| 3,426,011 A | 2/1969 | Parmerter | |
| 3,453,257 A | 7/1969 | Parmerter | |
| 3,453,259 A | 7/1969 | Parmerter | |
| 3,459,731 A | 8/1969 | Gramera et al. | |
| 4,235,871 A | 11/1980 | Papahadjopoulos et al. | |
| 4,605,735 A | 8/1986 | Miyoshi et al. | |
| 4,615,879 A | 10/1986 | Runge et al. | |
| 4,639,365 A | 1/1987 | Sherry | |
| 4,675,173 A | 6/1987 | Widder | |
| 4,687,658 A | 8/1987 | Quay | |
| 4,687,659 A | 8/1987 | Quay | |
| 4,709,037 A | 11/1987 | Sigler | |
| 4,711,955 A | 12/1987 | Ward et al. | |
| 4,737,323 A | 4/1988 | Martin et al. | |
| 4,751,313 A | 6/1988 | Levenson et al. | |
| 4,794,082 A | 12/1988 | Sigler | |
| 4,798,795 A | 1/1989 | Sigler | |
| 4,908,453 A | 3/1990 | Cocuzza | |
| 4,925,652 A | 5/1990 | Gries et al. | |
| 5,128,476 A | 7/1992 | Zhang et al. | |
| 5,134,127 A | 7/1992 | Stella et al. | |
| 5,180,828 A | 1/1993 | Ghazarossian et al. | |
| 5,252,743 A | 10/1993 | Barrett et al. | |
| 5,716,594 A | 2/1998 | Elmaleh et al. | |
| 6,120,751 A | 9/2000 | Unger | |
| 6,506,559 B1 | 1/2003 | Fire et al. | |
| 6,770,729 B2 | 8/2004 | Van Antwerp | |
| 7,056,704 B2 | 6/2006 | Tuschl et al. | |
| 8,669,236 B2 | 3/2014 | Elmaleh et al. | |
| 9,655,977 B2 | 5/2017 | Elmaleh | |
| 2003/0049203 A1 | 3/2003 | Elmaleh et al. | |
| 2003/0091640 A1 | 5/2003 | Ramanathan et al. | |
| 2005/0059028 A1 | 3/2005 | Nguyen et al. | |
| 2005/0136008 A1 | 6/2005 | Elmaleh et al. | |
| 2005/0245475 A1 | 11/2005 | Khvorova et al. | |
| 2005/0260757 A1 | 11/2005 | Gebeyehu et al. | |
| 2006/0223770 A1 | 10/2006 | Fougerolles et al. | |
| 2006/0257949 A1 | 11/2006 | Ross et al. | |
| 2009/0068106 A1 | 3/2009 | Corti et al. | |
| 2009/0104195 A1 | 4/2009 | Herman | |
| 2009/0220433 A1 | 9/2009 | Elmaleh et al. | |

(Continued)

FOREIGN PATENT DOCUMENTS

| | | |
|---|---|---|
| CA | 1 218 597 A | 3/1987 |
| CA | 1 253 514 A | 5/1989 |

(Continued)

OTHER PUBLICATIONS

English translation of WO2008013324, pp. 1-37, translated on Dec. 4, 2018 (Year: 2018).*

Adlerz et al., "Down-regulation of amyloid precursor protein by peptide nucleic acid oligomer in cultured rat primary neurons and astrocytes," Neuroscience Letters, 336:55-59 (2003).

Ambili et al., "siRNA Gene Therapy for Alzheimer's Disease Targeting App Gene," International Journal of Pharmacy and Pharmaceutical Sciences, 4(3):341-346 (2012).

Azorsa et al., "High-content siRNA screening of the kinome identifies kinases involved in Alzheimer's disease-related tau hyperphosphorylation," BMC Genomics, 11(25):1-10 (2010).

(Continued)

*Primary Examiner* — Brian Whiteman
(74) *Attorney, Agent, or Firm* — Foley Hoag LLP

(57) ABSTRACT

Described herein are compositions and methods for treating or imaging Alzheimer's disease (AD). The compositions comprise a biotin moiety and a siRNA moiety, without the need for a targeting agent such as an antibody, avidin, or streptavidin. In certain embodiments, the compositions further comprise a diagnostic agent.

12 Claims, 6 Drawing Sheets

Specification includes a Sequence Listing.

(56) References Cited

U.S. PATENT DOCUMENTS

| | | |
|---|---|---|
| 2011/0054160 A1 | 3/2011 | Manoharan et al. |
| 2011/0244561 A1 | 10/2011 | Davidson et al. |

FOREIGN PATENT DOCUMENTS

| | | | |
|---|---|---|---|
| CA | 1 341 176 C | 1/2001 | |
| DE | 3401052 A1 | 7/1984 | |
| DE | 3443252 A1 | 5/1986 | |
| DE | 3629194 A1 | 3/1987 | |
| EP | 071564 A1 | 2/1983 | |
| EP | 130934 A1 | 1/1985 | |
| EP | 133674 A1 | 3/1985 | |
| EP | 136812 A2 | 4/1985 | |
| EP | 165728 A1 | 12/1985 | |
| EP | 185899 A2 | 7/1986 | |
| EP | 186947 A1 | 7/1986 | |
| EP | 230893 A2 | 8/1987 | |
| EP | 232751 A1 | 8/1987 | |
| EP | 255471 A1 | 2/1988 | |
| EP | 292689 A2 | 11/1988 | |
| WO | WO-85/02772 A1 | 7/1985 | |
| WO | WO-85/04330 A1 | 10/1985 | |
| WO | WO-85/05554 A1 | 12/1985 | |
| WO | WO-85/05638 A1 | 12/1985 | |
| WO | WO-86/01112 A1 | 2/1986 | |
| WO | WO-87/01594 A1 | 3/1987 | |
| WO | WO-87/02893 A1 | 5/1987 | |
| WO | WO-88/00060 A1 | 1/1988 | |
| WO | WO-89/00557 A1 | 1/1989 | |
| WO | WO-89/06979 A1 | 8/1989 | |
| WO | WO-1996/14057 A1 | 5/1996 | |
| WO | WO-2003/010180 A1 | 2/2003 | |
| WO | WO-2005/037056 A2 | 4/2005 | |
| WO | WO-2006124726 A2 * | 11/2006 | ............ C12N 15/111 |
| WO | WO-2008013324 A1 * | 1/2008 | ......... A61K 31/7088 |

OTHER PUBLICATIONS

Boado et al., "Blood-Brain Barrier Transport for RNAi," Therapeutic Ribonucleic Acids in Brain Tumors, pp. 255-273 (2009).
Boado et al., "Drug Delivery of Antisense Molecules to the Brain for Treatment of Alzheimer's Disease and Cerebral Aids," Journal of Pharmaceutical Sciences, 87(11):1308-1315 (1998).
Faghihi et al., "Expression of a noncoding RNA is elevated in Alzheimer's disease and drives rapid feed-forward regulation of β-secretase," Nature Medicine, 14(7):723-730 (2008).
Fan et al., "Isolation of siRNA target by biotinylated siRNA reveals that human CCDC12 promotes early erythroid differentiation," Leukemia Research, 36:779-783 (2012).
Farah, Mohamed H., "RNAi Silencing in Mouse Models of Neurodegenerative Diseases," Current Drug Delivery, 4:161-167 (2007).
International Search Report dated Feb. 18, 2014, from PCT/US2013/057566.
Karpilow et al., "siRNA: Enhanced Functionality Through Rational Design and Chemical Modification," PharmaGenomics, March/April, pp. 32-40 (2004).
Kraynack et al., "Small interfering RNAs containing full 2'-O-methylribonucleotide-modified sense strands display Argonaute2/eIF2C2-dependent activity," Cold Spring Harbor Laboratory Press, 12:163-176 (2005).
Lash, Alex, "Beyond A-Beta: New Approaches to Alzheimer's," Start-Up, June, pp. 8-13 (2012).
Lovett-Racke et al., "Therapeutic Potential of Small Interfering RNA for Central Nervous System Diseases," Arch Neurol., 62(12):1810-1813 (2005).
Marine et al., "Activity profile-based siRNA screen to explore the functional genomics of Alzheimer's disease," Biotechniques, 43(6):1-6 (2007).
Miller et al., "Targeting Alzheimer's disease genes with RNA interference: an efficient strategy for silencing mutant alleles," Nucleic Acids Research, 32(2):661-668 (2004).

Richardson et al., "Mouse Models of Alzheimer's Disease: A Quest for Plaques and Tangles," ILAR Journal, 43(2):89-99 (2002).
Takemoto et al., "Role of Selenoprotein P in Alzheimer's Disease," Ethnicity & Disease, 20:S1-92-S1-95 (2010).
Uno et al., "High-Density Lipoprotein Facilitates in Vivo Delivery of α-Tocopherol-Conjugated Short-Interfering RNA to the Brain," Human Gene Therapy, 22:711-719 (2011).
Written Opinion of the International Search Authority PCT/US2013/057566, pp. 1-10, dated Nov. 21, 2013.
Xia et al., "Antibody-Mediated Targeting of siRNA via the Human Insulin Receptor Using Avidin-Biotin Technology," Molecular Pharmaceutics, 6(3):747-751 (2008).
Xia et al., "Intravenous siRNA of Brain Cancer with Receptor Targeting and Avidin-Biotin Technology," Pharmaceutical Research, 24(12):2309-2316 (2007).
Anonymous, "Alignment of seq 1 with APP transcript," XP055402078 (Aug. 29, 2017).
Anonymous, "FASTA sequence search of SEQ ID No. 1," XP055402080 (Aug. 29, 2017).
Agrawal et al., "Antisense therapeutics: is it as simple as complementary base recognition?" Mol Med Today, 6(2):72-81 (2000).
Bass, "The Short Answer," Nature, 411:428-429 (2001).
Berge et al., "Pharmaceutical Salts," J Pharm Sci, 66(1):1-19 (1977).
Billy et al., "Specific interference with gene expression induced by long, double-stranded RNA in mouse embryonal teratocarcinoma cell lines," Proc Natl Acad Sci USA, 98(25):14428-14433 (2001).
Boutla et al., "Short 5'-phosphorylated double-stranded RNAs induce RNA interference in Drosophila," Curr Biol, 11(22):1776-1780 (2001).
Brasch, "Work in progress: methods of contrast enhancement for NMR imaging and potential applications. A subject review," Radiology, 147(3):781-788 (1983).
Chirilia et al., "The use of synthetic polymers for delivery of therapeutic antisense oligodeoxynucleotides," Biomaterials, 23(2):321-342 (2002).
Crawford et al., "High speed reprojection and its applications," Proc SPIE 0914, Medical Imaging II, pp. 311-318 (1988).
Crooke, "Progress in Antisense Technology," Annu Rev Med, 55:61-95 (2004).
Davidson et al., "Molecular medicine for the brain: silencing of disease genes with RNA interference," Lancet Neurol, 3:145-149 (2004).
Dordunoo et al., "Preformulation studies on solid dispersions containing triamterene or temazepam in polyethylene glycols or Gelucire 44/14 for liquid filling of hard gelatin capsules," Drug Dev Ind Pharm, 17(12):1685-1713 (1991).
Doyle et al., "Relaxation Rate Enhancement Oserved in Vivo by NMR Imaging," J Comput Assist Tomogr, 5(2):295-296 (1981).
Elbashir et al., "Analysis of gene function in somatic mammalian cells using small interfering RNAs," Methods, 26(2):199-213 (2002).
Elbashir et al., "Duplexes of 21-nucleotide RNAs mediate RNA interference in cultured mammalian cells," Nature, 411(6836):494-498 (2001).
Elbashir et al., "Functional anatomy of siRNAs for mediating efficient RNAi in Drosophila melanogaster embryo lysate," EMBO J, 20(23):6877-6888 (2001).
Elbashir et al., "RNA interference is mediated by 21-and 22-nucleotide RNAs," Genes Dev, 15(2):188-200 (2001).
Elmaleh et al., "$^{99m}$Tc-labeled nucleotides as tumor-seeking radiodiagnostic agents," Proc Natl Acad Sci USA, 81:918-921 (1984).
Filleur et al., "siRNA-mediated inhibition of vascular endothelial growth factor severely limits tumor resistance to antiangiogenic thrombospondin-1 and slows tumor vascularization and growth," Cancer Res, 63(14):3919-3922 (2003).
Fire et al., "Potent and specific genetic interference by double-stranded RNA in Caenorhabditis elegans," Nature, 391:806-811 (1998).
Grosshans et al., "Micro-RNAs: small is plentiful," J Cell Biol, 156(1):17-22 (2002).

(56) References Cited

OTHER PUBLICATIONS

Hammond et al., "An RNA-directed nuclease mediates post-transcriptional gene silencing in *Drosophila* cells," Nature, 404:293-296 (2000).
Harborth et al., "Identification of essential genes in cultured mammalian cells using small interfering RNAs," J Cell Sci, 114(24):4557-4565 (2001).
Hutvágner et al., "A cellular function for the RNA-interference enzyme Dicer in the maturation of the let-7 small temporal RNA," Science 293:834-838 (2001).
Jang et al., "Gene delivery from polymer scaffolds for tissue engineering," Expert Rev Med Devic, 1(1):127-138 (2004).
Koutcher et al., "Contrast agents and spectroscopic probes in NMR," J Nucl Med, 25(4):506-513 (1984).
Krieg, "CpG motifs in bacterial DNA and their immune effects," Annu Rev Immunol, 20:709-760 (2002).
Lauterbur et al., "Augmentation of tissue water proton spin-lattice relaxation rates by in vivo addition of paramagnetic ions," Frontiers of Biological Energetics, Academic Press, 1:752-759 (1978).
Lauterbur, "Progress in n.m.r. zeugmatography imaging," Philos Trans R Soc Lond B Biol Sci, 289(1037):483-487 (1980).
Layzer et al., "In vivo activity of nuclease-resistant siRNAs," RNA, 10:766-771 (2004).
Lipardi et al., "RNAi as random degradative PCR: siRNA primers convert mRNA into dsRNAs that are degraded to generate new siRNAs," Cell, 107(3):297-307 (2001).
Mendonça-Dias et al., "Paramagnetic contrast agents in nuclear magnetic resonance medical imaging," Semin Nucl Med, 13(4):364-376 (1983).
Nilsson et al., "Antibody-bound amyloid precursor protein upregulates ornithine decarboxylase expression," Biochem Biophys Res Commun, 341(4):1294-1299 (2006).
Nykänen et al., "ATP requirements and small interfering RNA structure in the RNA interference pathway," Cell, 107(3):309-321 (2001).
Opalinska et al., "Nucleic-Acid Therapeutics: Basic Principles and Recent Applications," Nat Rev Drug Discov, 1:503-514 (2002).
Paddison et al., "Stable suppression of gene expression by RNAi in mammalian cells," Proc Natl Acad Sci USA, 99(3):1443-1448 (2002).
Parrish et al., "Functional anatomy of a dsRNA trigger: differential requirement for the two trigger strands in RNA interference," Mol Cell, 6(5):1077-1087 (2000).
Peracchi et al., "Prospects for antiviral ribozymes and deoxyribozymes," Rev Med Virol, 14:47-64 (2004).
Robertson et al., "The regulation of the protein kinase PKR by RNA," Biochimie, 78(11-12):909-914 (1996).

Runge et al., "Paramagnetic agents for contrast-enhanced NMR imaging: a review," AJR Am J Roentgenol, 141(6):1209-1215 (1983).
Runge et al., "Work in progress: potential oral and intravenous paramagnetic NMR contrast agents," Radiology, 147(3):789-791 (1983).
Senechal et al., "Amyloid precursor protein knockdown by siRNA impairs spontaneous alternation in adult mice," J Neurochem, 102(6):1928-1940 (2007).
Sheen et al., "Bioavailability of a poorly water-soluble drug from tablet and solid dispersion in humans," J Pharm Sci, 80(7):712-714 (1991).
Sijen et al., "On the role of RNA amplification in dsRNA-triggered gene silencing," Cell, 107(4):465-476 (2001).
Song et al., "RNA interference targeting Fas protects mice from fulminant hepatitis," Nat Med, 9(3):347-351 (2003).
Tolentino et al., "Intravitreal injection of vascular endothelial growth factor small interfering RNA inhibits growth and leakage in a nonhuman primate, laser-induced model of choroidal neovascularization," Retina, 24(I):132-138 (2004).
Van Uden et al., "Cyclodextrins as a useful tool for bioconversions in plant cell biotechnology," Plant Cell Tiss Org Cult, 38:103-113 (1994).
Weissleder et al., "Dual-contrast MR imaging of liver cancer in rats," AJR Am J Roentgenol, 150(3):561-566 (1988).
Weissleder et al., "Pyogenic liver abscess: contrast-enhanced MR imaging in rats," AJR Am J Roentgenol, 150(1):115-120 (1988).
Wenz, "Cyclodextrins as building blocks for supramolecular structures and functional units," Angew Chem Int Edit, 33:803-822 (1994).
Yang et al., "Evidence that processed small dsRNAs may mediate sequence-specific mRNA degradation during RNAi in *Drosophila* embryos," Curr Biol, 10(19):1191-1200 (2000).
Yang et al., "Specific double-stranded RNA interference in undifferentiated mouse embryonic stem cells," Mol Cell Biol, 21(22):7807-7816 (2001).
Zamore et al., "RNAi: double-stranded RNA directs the ATP-dependent cleavage of mRNA at 21 to 23 nucleotide intervals," Cell, 101:25-33 (2000).
Australian Examination Report for Application No. AU 2013308519 dated Mar. 22, 2019.
Boado et al., "Imaging gene expression in the brain with peptide nucleic acid (PNA) antisense radiopharmaceuticals and drug targeting technology," Letters in Peptide Science, 10:169-190 (2003).
Extended European Search Report from European Application No. 18179410 dated Mar. 22, 2019.
Pardridge, "Blood-brain barrier delivery of protein and non-viral gene therapeutics with molecular Trojan horses," Journal of Controlled Release, 122(3):345-348 (2007).
Partial Search Report for EP Patent Application 18179410.8 dated Dec. 17, 2018.

\* cited by examiner

Biotin does not merge with nuclei in normal cells.

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
ctagcaacca aaggagtaca a                                            21

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 2
gccauuaaga ucgcuuacut t                                              21

<210> SEQ ID NO 3
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
cuuacgcuga guacuucgau u                                              21

<210> SEQ ID NO 4
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ucgaaguacu cagcgusagu u                                              21

<210> SEQ ID NO 5
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
cuuacgcuga guacuucgau u                                              21

<210> SEQ ID NO 6
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ucgaaguacu cagcgusagu u                                              21

<210> SEQ ID NO 7
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Pseudouridine

<400> SEQUENCE: 7
ucuuacgcug aguacuucga uu                                             22
```

<210> SEQ ID NO 8
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 8
ucgaaguacu cagcgusagu u                                       21

<210> SEQ ID NO 9
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 9
caggactagt cttttaggtc aaaaagaaga agctttgtaa ccgttggttt ccgtagtgta    60

<210> SEQ ID NO 10
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 10
ttcgaaccgg ggacctttcg cgtgttaggc gaacgtgata accactacac tacggaaacc    60
aac                                                                 63

<210> SEQ ID NO 11
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 11
aaaaaaatga acttccccgt cagcttgcaa gcttccaagc tgacggggaa gttcatcttc    60
gaaccgggga cctttcg                                                  77

<210> SEQ ID NO 12
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 12
aaaaaagtgg ccaggtggaa gtaaaatcca agcttcgatt ttacttccac ctggccacct    60
tcg                                                                 63

<210> SEQ ID NO 13
<211> LENGTH: 77
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
aaaaaaggtg gccagatgga agtaaaccaa gcttcgttta cttccatctg gccacccttc      60
gaaccgggga cctttcg                                                    77

<210> SEQ ID NO 14
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
aaaaaatgaa gtgaagatgg atgcagccaa gcttcgctgc atccatcttc acttcacttc      60
gaaccgggga cctttcg                                                    77

<210> SEQ ID NO 15
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
aaaaaatgaa gtgaatctgg atgcagccaa gcttcgctgc atccagattc acttcacttc      60
gaaccgggga cctttcg                                                    77

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
ggtggccaga tggaagtaaa                                                 20

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
tgaagtgaat ctggatgcag                                                 20

<210> SEQ ID NO 18
<211> LENGTH: 23
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: modified_base
<222> LOCATION: (3)..(21)
<223> OTHER INFORMATION: a, c, t, g, unknown or other

<400> SEQUENCE: 18
aannnnnnnn nnnnnnnnnn ntt                                            23

<210> SEQ ID NO 19
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Biotin-C
<220> FEATURE:
<221> NAME/KEY: modified_base
<222> LOCATION: (21)..(21)
<223> OTHER INFORMATION: U-Dy547

<400> SEQUENCE: 19
cuuacgcuga guacuucgau u                                              21

<210> SEQ ID NO 20
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Dy547-C
<220> FEATURE:
<221> NAME/KEY: modified_base
<222> LOCATION: (21)..(21)
<223> OTHER INFORMATION: U-Biotin

<400> SEQUENCE: 20
cuuacgcuga guacuucgau u                                              21

<210> SEQ ID NO 21
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Biotin-U
<220> FEATURE:
<221> NAME/KEY: modified_base
<222> LOCATION: (21)..(21)
<223> OTHER INFORMATION: U-Dy547

<400> SEQUENCE: 21
ucgaaguacu cagcgusagu u                                              21
```

BIOTIN COMPLEXES FOR TREATMENT AND DIAGNOSIS OF ALZHEIMER'S DISEASE

RELATED APPLICATIONS

This application is a divisional application of U.S. patent application Ser. No. 14/421,022, which is the National Stage Application of PCT/US13/057566, filed Aug. 30, 2013, which claims the benefit of priority to U.S. Provisional Patent Application Ser. No. 61/695,487, filed Aug. 31, 2012, the contents of each of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Oct. 18, 2013, is named MAA-020.25_SL.txt and is 6,760 bytes in size.

BACKGROUND OF THE INVENTION

Alzheimer's disease (AD) is a progressive neurodegenerative disorder of the brain, which is characterized by the memory deterioration, behavioral disturbances, impairment of activities of daily living, and loss of independent function. It is thought that 18-24 million people in the world are currently suffering from AD, two-thirds of whom are living in developed or developing countries. This number is expected to reach 34 million by 2025.

Accumulation of insoluble aggregates of amyloid-beta peptide (Aβ) is thought to be a central mechanism for the pathogenesis of AD. Aβ peptides are generated from the cleavage of amyloid precursor protein (APP) by beta- and gamma-secretases. Cleavage of APP by BACE1 (Beta Amyloid Cleaving Enzyme-1) is believed to be a prerequisite for gamma-secretase-mediated processing.

A number of drugs aimed at inhibiting the accumulation of Aβ have failed in clinical trials. Other drugs that are still in clinical trials are also directed at inhibiting the accumulation of Aβ. However, most experts now believe that it may be too late to start Aβ inhibitory therapies after a patients shows symptoms.

For example, a mutant allele of the tau protein was targeted in vitro using shRNA plasmids, demonstrating that a single nucleotide mutation could be used to suppress mutant tau by siRNA. Dominantly inherited mutations in the tau gene may be targets in neurodegenerative diseases other than AD. Frontotemporal dementia with parkinsonism linked to chromosome 17 has mutations in tau, resulting in altered sequence or aberrant splicing. Abnormal expression of tau is also associated with progressive supranuclear palsy and corticobasal ganglionic degeneration.

Additional targets for AD include the apolipoprotein E ε4 allele (ApoE4), the secretases, and the presenilin genes. Together with increasing age, ApoE4 is considered the most significant risk factor for AD. Suppression of ApoE4 with siRNA could potentially reduce the probability of developing AD or delay its onset, at least in heterozygotes. Because ApoE4 plays a critical role in cholesterol and triglyceride transport, the risk-benefit ratio of gene targeting in ApoE4 homozygotes is less clear. More than 150 mutations have been identified in the presenilin genes, which result in an early-onset aggressive form of AD, Presenilin is the catalytic subunit of γ-secretase, and the mutations in presenilin enhance production of the highly self-aggregating Aβ42 peptide, which can be reversed by suppressing MAMA presenilin with siRNA. This leads to the question of whether the secretases could be the point of therapeutic intervention. Because β-secretase-deficient mice have no apparent deficits, this particular enzyme may be a good therapeutic target.

Accordingly, therapies directed to inhibiting tau proteins or other proteins involved in the process are gaining more attention. Under normal circumstances, tau helps build the microtubule structures in neurons. However in diseased brains, this long protein with more than 400 amino acids, misfolds and aggregates into tangles within neurons. Higher levels of tau in the cerebrospinal fluid are associated with advancing AD. It is thought that extracellular tau isn't detritus shed by dead neurons, but rather material secreted by diseased neurons, which acts as a disease transport, shuttling from neuron to neuron along the synapses and triggering more misfolding, more tangles and more neurotoxicity.

New therapies for Alzheimer's are needed.

SUMMARY OF THE INVENTION

In certain embodiments, the invention relates to a composition consisting essentially of a biotin moiety and a siRNA moiety.

In certain embodiments, the invention relates to a composition comprising a biotin moiety and a siRNA moiety. In certain embodiments, the composition does not comprise an antibody, an antigen, avidin, or streptavidin.

In certain embodiments, the invention relates to a composition consisting of a biotin moiety and a siRNA moiety.

In certain embodiments, the invention relates to any one of the aforementioned compositions, wherein the siRNA moiety is selected from the group consisting of: CTAG-CAACCAAAGGAGTACAA (SEQ ID NO:1), GCCAUUAAGAUCGCUUACUtt (SEQ ID NO:2), CUUACGCUGAGUACUUCGAUU (SEQ ID NO:3), UCGAAGUACUCAGCGUSAGUU (SEQ ID NO:4), CUUACGCUGAGUACUUCGAUU (SEQ ID NO:5), UCGAAGUACUCAGCGUSAGUU (SEQ ID NO:6), PCUUACGCUGAGUACUUCGAUU (SEQ ID NO:7), and UCGAAGUACUCAGCGUSAGUU (SEQ ID NO:8), or a nucleic acid that has at least 85% sequence homology with any one of SEQ ID NOS:1-15.

In certain embodiments, the invention relates to a pharmaceutically acceptable formulation, wherein the pharmaceutically acceptable formulation comprises a therapeutically-effective amount of any one of the aforementioned compositions and a pharmaceutically acceptable carrier or diluent.

In certain embodiments, the invention relates to a method of treating Alzheimer's disease in a mammal, comprising the step of:

administering to said mammal a therapeutically effective amount of any one of the aforementioned compositions.

In certain embodiments, the invention relates to a method generating an image of a subject, comprising the steps of:

administering to a subject in need of imaging a detectable amount of any one of the aforementioned compositions, and generating an image.

DETAILED DESCRIPTION OF THE INVENTION

Compositions of the Invention

Figure 1:
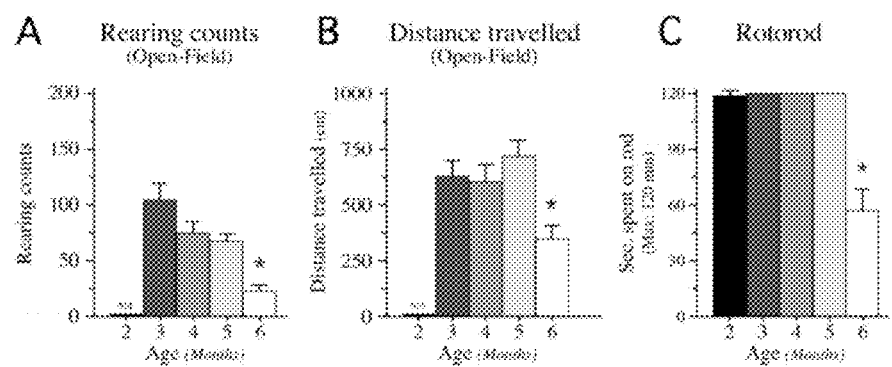
FIG. 1 depicts the behavioural progression in human P301S Tau transgenic mice. Mice overexpressing human Tau with the P301S mutation show deficits in rearing behaviour, which significantly progresses over time (A). Deficits can also be picked up in ambulation as distanced travelled, in the open-Field (B) and the performance in rotorod test (C). These severe and significant deficits can be observed at an age of 6 months. * different from all other timepoints. One-way ANOVAs F(3,59)=4.9635, 11.199, and 28.409 followed by each pair student's t-tests for A, B and C respectively. p<0.004 for all comparisons.

In general, the invention features novel compositions comprised of biotin and an siRNA sequence with or without a linker. In certain embodiments, the compositions consist essentially of a biotin moiety and a siRNA moiety. As used herein, "siRNA" refers to a double stranded RNA or single stranded RNA that can enter a RISC (RNAi-induced silencing complex) and does not induce a deleterious interferon response in a human cell, e.g., it has a duplexed region of less than 60 but preferably less than 50, 40, or 30 nucleotide pairs. The siRNA or a cleavage product thereof can down regulate a target gene, e.g., by inducing RNAi with respect to a target RNA, preferably an endogenous or pathogen target RNA. siRNA are known to silence protein production.

"Conjugated" or "linked" as used herein means ionically or, preferably, covalently attached (e.g., via a crosslinking agent).

In certain embodiments, the compositions of the invention do not comprise a targeting moiety, such as an antibody, an antigen, avidin, or streptavidin; the compositions are able to target cells without the need for these traditional targeting moieties.

In certain embodiments, the compositions of the invention are able to transfect cells in vivo. In certain embodiments, biotin alone acts as a delivery probe for the siRNA moiety.

Compositions described herein may partially, substantially, or completely delete, silence, inactivate, interfere with, or down-regulate a gene that encodes a protein involved in AD pathogenesis. The protein involved in AD pathogenesis, may be an amyloid precursor protein (APP), beta amyloid cleaving enzyme-1 (BACE1), Tau, presenilin (for example, presenilin 1 (PS1) or presenilin 2 (PS2)), selenoprotein P (SelP), apolipoprotein E (ApoE), insulin-degrading protein, neprilysin, or alpha-synuclidin. In certain embodiments, the siRNA interferes in any process that produces Aβ, or causes the aggregation of Aβ. In certain embodiments, the siRNA interferes with any process that produces Tau fibrilly tangles.

In certain embodiments, the gene is selected from the group consisting of MARK2, PAK3, PAK2, ADCK5, AKAP13, LOC55971, PLK2, DYRK1A, MAK, ITK, PIM1, RAGE, ITPK1, CKB, PFKM, DGKB, and SPHK2. In certain embodiments, the gene is selected from the group consisting of EIF2AK2, CDKL1, DCK, DGKQ, PFKFB3, ERK8, STK19, PRKG2, and PAM2K1IP1.

The siRNA moiety may be comprised of a sense strand and an antisense strand; the sense strand comprising a 3' end and a 5' end; and the antisense strand comprising a 3' end and a 5' end.

"Antisense" nucleic acids refer to nucleic acids that specifically hybridize (e.g., bind) with a complementary sense nucleic acid, e.g., cellular mRNA and/or genomic DNA, under cellular conditions so as to inhibit expression (e.g., by inhibiting transcription and/or translation). The binding may be by conventional base pair complementarity or, for example, in the case of binding to DNA duplexes, through specific interactions in the major groove of the double helix.

A biotin moiety may be attached to a sense strand. Alternatively, a biotin moiety may be attached to an antisense strand. Attachment may occur at the 3' or 5' end of either strand. In certain embodiments, the composition comprises more than one biotin moiety.

Compositions comprised of a biotin and siRNA may further include a diagnostic agent, e.g. a composition capable of generating a detectable image upon binding with a target. Examples include fluorophores (e.g. Dy547), chromophores, chemoluminescing agents, radionuclides (e.g., In-111, Tc-99m, I-123, I-125 F-18, Ga-67, Ga-68, and for Positron Emission Tomography (PET) and Single Photon Emission Tomography (SPECT), unpair spin atoms and free radicals (e.g., Fe, lanthanides, and Gd) and contrast agents (e.g., chelated (DTPA) manganese) for Magnetic Resonance Imaging (MRI). In certain embodiments, the composition is of the format siRNA-biotin-diagnostic agent or diagnostic agent-siRNA-biotin.

Appropriate siRNA moieties may include any of the sequences identified herein. In certain embodiments, the siRNA moiety comprises: CTAGCAACCAAAGGAGTA-CAA (SEQ ID NO:1), GCCAUUAAGAUCGCUUACUtt (SEQ ID NO:2), CUUACGCUGAGUACUUCGAUU (SEQ ID NO:3), UCGAAGUACUCAGCGUSAGUU (SEQ ID NO:4), CUUACGCUGAGUACUUCGAUU (SEQ ID NO:5), UCGAAGUACUCAGCGUSAGUU (SEQ ID NO:6), PCUUACGCUGAGUACUUCGAUU (SEQ ID NO:7), UCGAAGUACUCAGCGUSAGUU (SEQ ID NO:8), any of SEQ ID NO:9-15, or a nucleic acid that has at least 85%, 90%, 95% or 99% sequence homology with any one of SEQ ID NOS:1-15.

In certain embodiments, the siRNA moiety comprises GGTGGCCAGATGGAAGTAAA (SEQ ID NO: 16), or a sequence fully complementary to GGTGGCCAGATGGAAGTAAA (SEQ ID NO: 16).

In certain embodiments, the siRNA moiety comprises TGAAGTGAATCTGGATGCAG (SEQ ID NO: 17), or a sequence fully complementary to TGAAGTGAATCTGGATGCAG (SEQ ID NO: 17).

In certain embodiments, aspects of the invention are described in U.S. Patent Application Publication No. 2011/0244561, which is hereby incorporated by reference in its entirety.

The siRNA moiety may further include a guanosine at the 5'-end.

The sense and/or antisense strands of the siRNA moiety may equal to or less than 30, 25, 24, 23, 22, 21, 20, 19, 18 or 17 nucleotides in length. An siRNA moiety may include one or more overhangs. For example, the siRNA moiety may include one or two 3' overhangs of 2-3 nucleotides. In certain embodiments, the invention relates to any one of the aforementioned compositions, wherein the siRNA moiety is composed of 21-nt sense and 21-nt antisense strands, paired in a manner to have a 19-nucleotide duplex region and a 2-nt 3' overhang at each 3' terminus. In certain embodiments, the invention relates to any one of the aforementioned compositions, wherein the 2-nt 3' overhang is either UU or dTdT. Symmetric 3'-overhangs ensure that the sequence-specific endonuclease complexes (siRNPs) are formed with approximately equal ratios of sense and antisense target RNA cleaving siRNPs. The 3'-overhang in the sense strand provides no contribution to recognition as it is believed the antisense siRNA strand guides target recognition. Therefore, the UU or dTdT 3'-overhang of the antisense sequences is complementary to the target mRNA but the symmetrical UU or dTdT 3'-overhang of the sense siRNA oligo does not need to correspond to the mRNA. The use of deoxythymidines in both 3'-overhangs may increase nuclease resistance, although siRNA duplexes with either UU or dTdT overhangs work equally well. 2'-Deoxynucleotides in the 3' overhangs are as efficient as ribonucleotides, but are often cheaper to synthesize.

The targeted region in the mRNA, and hence the sequence in the siRNA duplex, are chosen using the following guidelines. The open reading frame (ORF) region from the cDNA sequence is recommended for targeting, preferably at least 50 to 100 nucleotides downstream of the start codon, most preferably at least 75-100. Both the 5' and 3' untranslated regions (UTRs) and regions near the start codon are not recommended for targeting as these may be richer in regulatory protein binding sites. UTR-binding proteins and/or translation initiation complexes may interfere with binding of the siRNP endonuclease complex.

The sequence of the mRNA or cDNA is searched seeking the sequence AA(N19)TT (SEQ ID NO: 18). Sequences with approximately 50% G/C-content (30% to 70%) are used. If no suitable sequences are found, the search is extended to sequences AA(N21). The sequence of the sense siRNA corresponds to 5'-(N19)dTdT-3' or N21, respectively. In the latter case, the 3' end of the sense siRNA is converted to dTdT. The rationale for this sequence conversion is to generate a symmetric duplex with respect to the sequence composition of the sense and antisense 3' overhangs. It is believed that symmetric 3' overhangs help to ensure that the siRNPs are formed with approximately equal ratios of sense and antisense target RNA-cleaving siRNPs. The modification of the overhang of the sense sequence of the siRNA duplex is not expected to affect targeted mRNA recognition, as the antisense siRNA strand glides target recognition.

If the target mRNA does not contain a suitable AA(N21) sequence, it is recommended to search for NA(N21) The sequence of the sense and antisense strand may still be synthesized as 5' (N19)TT as the sequence of the 3' most nucleotide of the antisense siRNA does not appear to contribute to specificity.

It is further recommended to search the selected siRNA sequence against EST libraries in appropriate databases (e.g., NCBI BLAST database search) to ensure that only one gene is targeted.

The appropriately designed siRNAs are either obtained from commercial sources (such as Dharmacon Research, Lafayette, Colo.; Xergon, Huntsville, Ala.; Ambion, Austin, Tex.) or chemically synthesized used appropriately protected ribonucleoside phosphoramidites and a conventional DNA/RNA synthesizer according to standard protocols. The RNA oligonucleotides are 2'-deprotected, desalted and the two strands annealed, according to manufacturer's specifications or conventional protocols, depending on how the siRNAs are obtained. All handling steps are conducted under strict sterile, RNase-free conditions.

As used herein, "biotin moiety" encompasses biotin (hexahydro-2-oxo-1H-thieno[3,4-d]imidazole-4-pentanoic acid); a 244 dalton vitamin, analogs and derivatives thereof, as well as compounds comprising multiple biotin moieties. Exemplary biotin analogs that may be used in the compositions of the invention are described in U.S. Pat. No. 5,716,594 by Elmaleh, et al, which patent is hereby incorporated by reference in its entirety and exemplary compounds comprising multiple biotin moieties (e.g., "polybiotin compounds") that may be used in the compositions of the invention are described in U.S. Ser. No. 10/956,687, "Polybiotin Compounds for Magnetic Resonance Imaging and Drug Discovery" filed Oct. 1, 2004, by Elmaleh, et al., which application is hereby incorporated by reference in its entirety. Patents and literature are replete with other exemplary biotin moieties including various spacers, linking groups and the like, for use in the present applications. Nonlimiting examples can be found in M. D. Savage, et al. (1992), Pierce Chemical Co., Avidin-Biotin Chemistry: A Handbook; DE 3629194, U.S. Pat. Nos. 5,180,828, 4,709,037 and 5,252,743, 4,798,795, 4,794,082, WO 85/05638 all incorporated herein by reference.

Methods of conjugating biotin moieties to other chemical entities (i.e., methods of biotinylation) are well-known in the art. For example, a biotin moiety (which can be any desired biotin compound optionally with spacer arm and/or leaving group) such as N-hydroxysuccinimide-biotin (NHS-biotin) can be reacted with the desired biomolecule, e.g., the scaffold, in a solvent and in the presence of a buffer. The NHS functions as a leaving group to provide the so-formed biotinylated scaffold. This can be purified using standard methodology, for example, subjecting the biotinylated scaffold to purification on a Sephadex™ chromatography column to remove free biotin, NHS-biotin and other low molecular weight solutes. Many methods for conjugating biotin moieties to oligonucleotides have been described in the art as well. See, for example, U.S. Pat. Nos. 5,128,476, 4,605,735, 4,751,313, 4,711,955, and 4,908,453.

To allow coupling of siRNAs, biotin, and/or linker molecules, the surface chemical groups can be derivatized with carboxyl (COOH), amino ($NH_2$), hydroxyl (OH), hydrazide ($NHNH_2$), amide ($CONH_2$), chloromethyl ($CH_3Cl$), and aldehyde (COH) groups. Such strategies for derivatizing and modifying various chemical groups (such as surface hydroxyl or amino groups) to allow coupling of lipids, carbohydrates, peptides, peptidomimetics, peptide-nucleic acids (PNAs), proteins, small molecules, natural products and oligonucleotides to a surface are well-known in the art.

Linkers (also known as "linker molecules" or "cross-linkers" or "spacers") may be used to conjugate the biotin moiety and siRNA moiety. The majority of known cross-linkers react with amine, carboxyl, and sulfhydryl groups. Linker molecules may be responsible for different properties of the composition. The length of the linker should be considered in light of molecular flexibility during the conjugation step, and the availability of the conjugated molecule for its target. Longer linkers may thus improve the biological activity of the compositions of the invention, as well as the ease of preparation of them. The geometry of the linker may be used to orient a molecule for optimal reaction with a target. A linker with flexible geometry may allow the entire biotinylated composition to conformationally adapt as it binds a target sequence. The nature of the linker may be altered for other various purposes. For example, the hydrophobicity of a polymeric linker may be controlled by the order of monomeric units along the polymer, e.g. a block polymer in which there is a block of hydrophobic monomers interspersed with a block of hydrophilic monomers.

The chemistry of preparing and utilizing a wide variety of molecular linkers is well-known in the art and many pre-made linkers for use in conjugating molecules are commercially available from vendors such as Pierce Chemical Co., Roche Molecular Biochemicals, United States Biological. Exemplary linker molecules for use in the compositions of the invention include, but are not limited to: aminocaproic acid (ACA); polyglycine, and any other amino acid polymer, polymers such as polyethylene glycol (PEG), polymethyl methacrylate (PMMA), polypropylene glycol (PPG); homobifunctional reagents such as APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS; heterobifunctional reagents such as ABH, AEDP, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, MBuS, M2C2H, MPBH, MSA, NHS-ASA, PDPH, PMPI, SADP, SAED. SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS. Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS; and trifunctional linkers such as Sulfo-SBED, THPP β-[Tris(hydroxymethyl) phosphino] propionic acid (betaine) Any linkers contemplated for use include, but are not limited to, any molecule that does not contain a functionality incompatible with biotinylation the siRNA.

Branched linkers may be prepared or used so that multiple moieties per linker are able to react. Such multiply reactive linkers allow the creation of multimeric binding sites.

An appropriate linker may be a macromolecular polymer. Any of the above-mentioned polymers may comprise the macromolecular polymer. In certain embodiments, such macromolecular polymers may be comprised entirely of one type of polymeric molecule. In other embodiments, the macromolecular polymers may be comprised of more than one type of polymeric molecule. The macromolecular polymers may exist in many possible structures, for example, linear, comb-branched, dendrigraft, dendrimer, or a linear dendron architectural copolymer. For example, PEG and PPG may be used to create a variety of bi- and multivalent linkers. Methods of synthesizing, activating, and modifying branched PEG/PPG polymers and PEG/PPG block co-polymers are well-known in the art. PEG is hydrophilic, while PPG is hydrophobic. For instance, a linker could be synthesized with a PPG core and PEG branches.

Biotinylated siRNA may additionally include a diagnostic or therapeutic agent, e.g. an antibiotic, anti-viral, antifungal) or radionuclide (e.g. F-18, I-124, I-123, I-125, I-131, Re-186, Re-188, Y-90, Bi-212, At-211, Sr-89, Ho-166, Sm-153, Cu-67 and Cu-64). The term diagnostic agent refers to a composition capable of generating a detectable image upon binding with a target, for example, a fluorescent moiety, a chromophore, a radionuclide or a metal atom. In certain embodiments, the diagnostic agent contains a radionuclide such as In-111, Tc-99m, I-123, I-125 F-18, Ga-67, or Ga-68. The diagnostic agent may be visualized using Positron Emission Tomography (PET) or Single Photon Emission Tomography (SPECT). In other embodiments, the diagnostic agent is an unpaired spin atom or free radical (e.g. Fe or Gd) or contrast agent (e.g. chelated (DTPA) manganese) for Magnetic Resonance Imaging (MRI). Additional diagnostic agents for Magnetic Resonance Imaging and fluorescent imaging are described in the discussion below under the sections Contrast Agents and Fluorescent Imaging.

In certain embodiments, said metal atom is selected to give the complex superior properties as a MRI contrast agent. In certain embodiments, said metal atom is In-111, Tc-99m, I-123, I-125 F-18, Ga-67, or Ga-68. In certain embodiments, the metal atom is Y-90, Tc-99m, Re-188, P-32, Ho-166, Pd-109, La-140, Sm-153, Dy-165, or Er-169. In certain embodiments, the metal atom is $Gd^{3+}$, $Mn^{2+}$, $Fe^{3+}$, $Cr^{3+}$, dysprosium, holmium, or erbium.

Methods of Therapy or Diagnostic Imaging

One aspect of the invention relates to a method of treating Alzheimer's disease in a mammal, comprising the step of:

administering to said mammal a therapeutically effective amount of any one of the aforementioned compositions.

In certain embodiments, the invention relates to any one of the aforementioned methods, wherein said mammal is a human.

Biotinylation of siRNA allows for more effective intracellular delivery of the siRNA molecule, e.g. for more effective silencing. Such compositions are useful in the delivery or targeting of therapeutic or diagnostic agents, for example delivery or targeting of iRNA and antisense agents. Furthermore, biotin-containing compositions are preferentially adsorbed into troubled or unhealthy cells as compared to healthy cells. In addition, siRNA-containing compositions show a similar preference for uptake in unhealthy cells.

The language "effective amount" of a targeted therapeutic agent or imaging agent refers to that amount necessary or sufficient to eliminate, reduce, or maintain (e.g., prevent the spread of) an infection, tumor, or other target. The effective amount can vary depending on such factors as the disease or condition being treated, the particular targeted constructs being administered, the size of the subject, or the severity of the disease or condition. One of ordinary skill in the art can empirically determine the effective amount of a particular compound without necessitating undue experimentation.

In certain embodiments, the invention relates to the selection of a gene to be targeted for silencing, by degradation of its corresponding mRNA, such that expression of that gene is inhibited. Genes appropriate for use include those that are known to increase the presence of Aβ in a cell. For example, genes of interest are those that encode for amyloid precursor protein (APP), beta amyloid cleaving enzyme-1 (BACE1), Tau, a Presenilin (for example, presenilin 1 (PS1) or presenilin 2 (PS2)), selenoprotein P (SelP), apolipoprotein E (ApoE), insulin-degrading protein, neprilysin, or alpha-synuclidin. In certain embodiments, the siRNA interferes in any process that produces Aβ, or causes the aggregation of Aβ. In certain embodiments, the siRNA interferes with any process that produces Tau fibrilly tangles.

The method further includes the step of selecting a target sequence in the target mRNA and design of the siRNA duplexes for the target mRNA. Target sequence selection and siRNA duplex design is based on the guidelines of Tuschl et al., as have become standard in the art (Tuschl, T., P. D. Zamore, R. Lehmann, D. P. Bartel and P. A Sharp Genes Dev 13: 3191-3197 (1999); The siRNA user guide [www.mpibpc.gwdg.de/abteilu-ngen/100/105/sima.html]; Elbashir S M, Harborth J, Weber K, Tuschl T. Methods February; 26(2):199-213, (2002); Technical Bulletin #003-Revision B, Dharmacon Research, Inc. Lafayette, Colo., 2002).

Examples of siRNA screening of kinases involved in Tau hyperphosphorylation are described in Azorsa et al. *BMC Genomics* 2010, 11, 25, which is hereby incorporated by reference in its entirety. These siRNA will be derivatized with biotin to produce the siRNA-biotin conjugates of the invention, which deliver drug to the appropriate transformed or unhealthy cells.

Examples of methods for producing siRNA against targeted regions of genes encoding for APP or Tau are described in Miller, V. M., et al. *Nucleic Acids Res.* 2004, 32(2), 661-668, which is hereby incorporated by reference in its entirety. These siRNA will be derivatized with biotin to produce the siRNA-biotin conjugates of the invention, which deliver drug to the appropriate transformed or unhealthy cells.

Examples of siRNA that targets BACE1 are described in Singer, O., et al. *Nature Neuroscience* 2005, 8, 1343-1349, which is hereby incorporated by reference in its entirety.

Examples of screens for siRNA against PS1 are described in Kandimalla, R. J. L., et al. *J. Biomed. Sci.* 2012, 19, 2, which is hereby incorporated by reference in its entirety. These siRNA will be derivatized with biotin to produce the siRNA-biotin conjugates of the invention, which deliver drug to the appropriate transformed or unhealthy cells.

Examples of siRNA against SelP are described in Takemoto, A. S., et al. *Ethnicity &Disease* 2010, 20, SI-92, which is hereby incorporated by reference in its entirety. These siRNA will be derivatized with biotin to produce the siRNA-biotin conjugates of the invention, which deliver drug to the appropriate transformed or unhealthy cells.

Examples of siRNA that targets the APP gene are described in Ambili, T. R., et al. *Int. J. Pharmacy and Pharmaceutical Sci.* 2012, 4(3), 341, which is hereby incorporated by reference in its entirety. These siRNA will be derivatized with biotin to produce the siRNA-biotin conjugates of the invention, which deliver drug to the appropriate transformed or unhealthy cells.

Examples of a regulatory noncoding RNA that controls BACE1 mRNA expression are described in Faghihi, M. A., et al. *Nature Medicine* 2008, 14(7), 723, which is hereby incorporated by reference in its entirety. These siRNA will be derivatized with biotin to produce the siRNA-biotin conjugates of the invention, which deliver drug to the appropriate transformed or unhealthy cells.

Examples of an siRNA screen of 15,200 genes for effects on the processing of APP are described in Marine, S., et al. *BioTechniques* 2007, Supplement to Vol 43, xxii, which is hereby incorporated by reference in its entirety. These siRNA will be derivatized with biotin to produce the siRNA-biotin conjugates of the invention, which deliver drug to the appropriate transformed or unhealthy cells.

Another aspect of the invention relates to a method generating an image of a subject, comprising the steps of administering to a subject in need of imaging a detectable amount of any one of the aforementioned compositions comprising a diagnostic agent, and generating an image. For example, siRNA-biotin-diagnostic agent or diagnostic agent-siRNA-biotin (where the diagnostic agent is a tag such as a fluorophore) could be incubated with amyloid beta or brain slices and developed for image production for in vitro or ex vivo AD diagnostic purposes. Alternatively, siRNA-biotin-diagnostic agent or diagnostic agent-siRNA-biotin (where the diagnostic agent is a radionuclide) could be administered to mammals; then, brain uptake and kinetic behavior could be used for AD diagnosis. Normal brain areas will appear different from diseased regions of the brain.

In certain embodiments, said compound comprises at least one biotin group. In certain embodiments, said compound comprises at least two biotin groups. In certain embodiments, said diagnostic agent comprises a metal, and said method involves MRI. In certain embodiments, said diagnostic agent comprises $Gd^{3+}$, $Mn^{2+}$, $Fe^{3+}$, or $Cr^{3+}$.

In certain embodiments, the invention relates to any one of the aforementioned methods, wherein said subject is a human.

Pharmaceutical Compositions

In another aspect, the present invention provides pharmaceutically acceptable compositions which comprise a therapeutically-effective amount of one or more of the biotinylated compositions described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Kits

In certain embodiments, the invention relates to a kit for treating or imaging Alzheimer's Disease. For example, a kit may comprise one or more biotinylated compositions as described above and optionally instructions for their use. In still other embodiments, the invention provides kits comprising one or more pharmaceutical or diagnostic compositions and/or one or more devices for accomplishing administration of such compositions. For example, a subject kit may comprise a pharmaceutical or diagnostic composition and catheter for accomplishing direct injection.

EXEMPLIFICATION

The invention now being generally described, it will be more readily understood by reference to the following examples which are included merely for purposes of illustration of certain aspects and embodiments of the present invention, and are not intended to limit the invention.

Example 1

```
                                          (SEQ ID NO: 19)
5'-Biotin-CUUACGCUGAGUACUUCGAUU-Dy547-3'
```

Example 2

```
                                          (SEQ ID NO: 20)
5'-Dy547-CUUACGCUGAGUACUUCGAUU-Biotin-3'
```

Example 3

```
                                          (SEQ ID NO: 21)
5'-Biotin-UCGAAGUACUCAGCGUSAGUU-Dy547-3'
```

Example 4—Cell Uptake In Vivo

The biotin-siRNA compositions were added at 50 nM and cultured for 4 hours then 20 ul of FBS was added to continue culture for 40 h. Wells were washed with PBS and incubated with Hoechest (1 ug/ml) as a nuclei counterstaining Images of Dy547 (red), Hoechst (blue) and phase contrast were captured using a fluorescent microscope controlled by the Openlab imaging software, which merged three images. Bioluminescence was assayed for the two best siRNA oligos from the fluorescent study. A549Luc cells were plated at 5,000 cells per well of 96 well plate. The siRNA's were incubated at 5, 50 and 250 nM in serum free media (50 ul/well) for 4 hours then regular culture media (10% FBS in D'MEM) was added to 200 ul and cultured for 2 days. Cells were washed with fresh media and Luciferine was added at 0.5 mg/ml. Luminescence was read using an M5 plate reader (Molecular Devices). Assays were in triplicate and mean values plotted. See FIGS. 4-7.

Example 5

We have here suggested and experimentally worked on a siRNA interference technique to knockdown mutated and malign expression of human tau protein. For this we have characterized a transgenic mouse model expressing the human P301S mutation in the tau gene. Allen, B. et al. J Neurosci 22, 9340-51 (2002). This model shows tau aggregation and following severe behavioural impairment, in particular, in motor behaviours. The symptoms are subtle and non-significant in early adulthood, but can be picked up in test such as spontaneous rearing behaviour (FIG. 1A).

This behaviour gradually declines in this model over months, reaching significant at 6 months of age, as compared to early adulthood at 3 months. After 5-6 months the animals also show severe signs of paralysis, in particular, in the hindlimbs. These behaviours can be observed visually and readily pick up in behavioural tests measuring distance travelled (in open-field conditions; FIG. 1B) and time spend on a rotating rod (Rotorod test; FIG. 1C). These data provide us with important information about the model, which test paradigm to use, and at which time-points significant behavioural effects, of treatments strategies like siRNA interference of the tau protein, can be evaluated.

In order to deliver the siRNA in to cells several techniques has been suggested and tested with various successes. We have here investigated multiple transfection agents in vitro and Polyethylenelmine (PEI)-based and Accell-siRNA (Dharmacon) based delivery in vivo. First, we evaluated siRNA interference efficacy of the enhanced Green Flourescent Protein (eGFP) and the house-keeping protein Glyceraldehyde 3-phosphate dehydrogenase (GAPDH) using "naked" siRNA molecules. We used several transfection agents including Hi-Perfect (Quigen), Dharmafect (Dharmacon), X-treme Gene (Roche), Saint-RED (Synvolux), Trans-TKO (Mirus) and Interferrin (Polyplus). We prepared and used primary cortical cultures from E15-17 Actin-eGFP transgenic and C57/B6 embryos, as well as human mesenchephalic cell culture (LuhMes).

Figure 2:
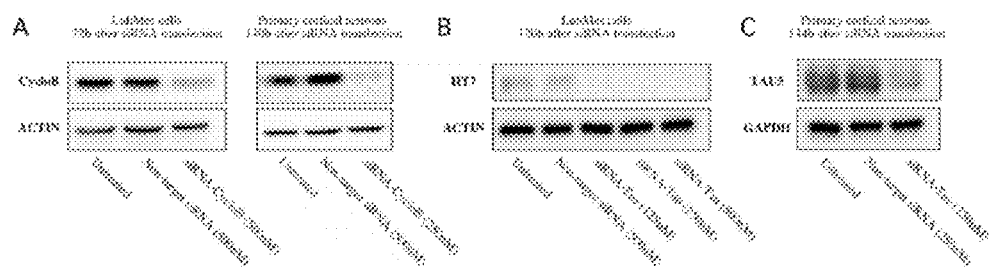
FIG. 2 depicts Accell-siRNA knockdown of Cyclophilin B and Tau protein in vitro. (A) Cyclophilin B (CycloB) was effectively knocked down in human mesencephalic neurons (LuhMes; 70% at 500 nM) and mouse primary cortical neurons (80% at 250 nM) at 72 and 140 h after transfection, respectively. (B-C) Similar, Accell-siRNA against human TAU showed significant knockdown in LuhMes (>95% at 125-500 nM; B) and primary cortical neurons (75% at 250 nM; C), derived from P301S mouse model, here shown at 120 and 144 h after siRNA transfection.

Further, we started to work with Lipofectamine 2000 (Invitrogen) as transfection agent, in which the Prof. Culmsee had experience. We used here both "naked" and modified (ON-TARGETplus, Dharmacon) siRNA against the homekeeping genes GAPDH and Cyclophilin B (CycloB) in primary cortical cell cultures expressing P301S mutation, derived from our transgenic P301S mutant Tau mice as well as LuhMes cells and mouse neuroblastoma cells (HT22). We also predicted good siRNA sequences for the human MAPT gene using the Whitehead's siRNA prediction tool (jura.wi.mit.edu/bioc/siRNAext/home.php). We designed siRNAs that targeted human mutant P301S tau, with a less affinity endogenous mouse tau, targeting the heterogene sequences between the human and the mouse MAPT genes. Four sequences were selected due to their poor overlap with the mouse tau gene and relative low overlap with any mouse genes. Although, using single or pools of GAPDH or CycloB, or the four Tau sequences alone or in a pool, we were not able to produce any consistent knockdown using Lipofectamine 2000. As the primary goal was to knockdown the protein level, we used western blot as the primary technique, rather than systematically looking at the RNA levels. As the transfection agent did not produce any reliable and consistent protein knock-down, we started to experimentally test the novel AccellsiRNA developed by Dharmacon. The Accell-siRNAs have been modified to enter the cell without any transfection agent, which also is more suitable for in vivo application. We tested Accell-siRNA in both primary neuronal cortical cultures as well as the LuhMes cells. Here, we were able to show that GAPDH and CycloB proteins could significant be knocked down in both cell types, as shown by western blot (FIG. 2A). The more potent protein knockdown, for both tested cells, was observed for CycloB. Furthermore, we also tested pre-designed Accell-siRNA against Tau protein (smartPool of four sequence). Similar, we were here able to significantly knockdown the human and mouse Tau protein both in primary cortical neurons at concentrations low as 250 nM siRNA (60-95%; FIG. 2C) and human mesencepahlic (LuhMes) cells at 125 nM (75-95%; FIG. 2D). Substantial protein knockdown was observed already at 72 h post transfection in the LuhMes cells and at 96 to 144 h in the primary neurons.

Figure 3:
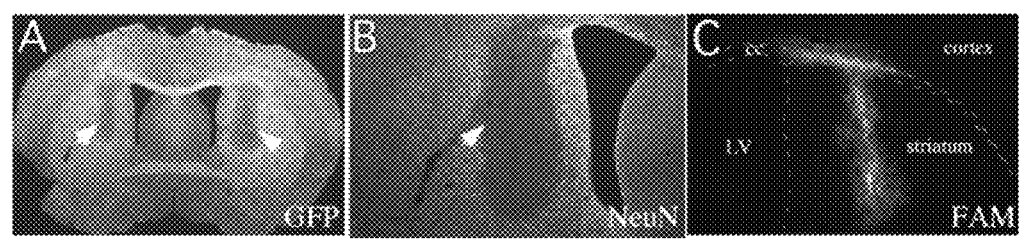
FIG. 3 depicts PEI-siRNA delivery to the striatum of Actin-eGFP expressing mice and Accell-siRNA transfection in C57/B6 mice. (A) Animals received single injections of PEI-siRNA-GFP (white arrow in right striatum) and PEI-Luciferace (white arrow in left striatum), where you can see a absence of GFP staining on both sides. Moreover, in the NeuN staining. (B) you can clearly appreciate the neuronal cell loss from the PEI-injection in the striatum (white arrow). (C) Single injection of Accell-siRNA couple with the fluorescence tag FAM showed robust transfection of the neurons in the striatum and in corpus callosum (cc) and cortex after 72 h.
Figure 4:
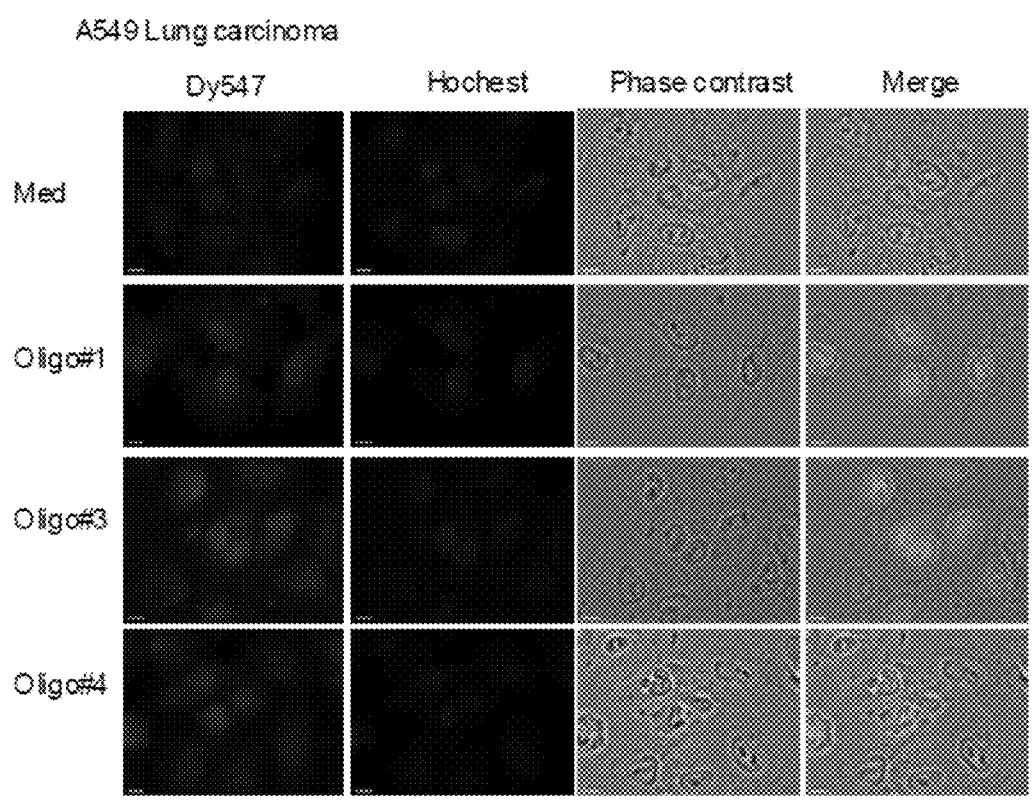
FIG. 4 is an image of A549 lung carcinoma cells transfected by oligonucleotides #1, #3 and #4 as described herein.
Figure 5:
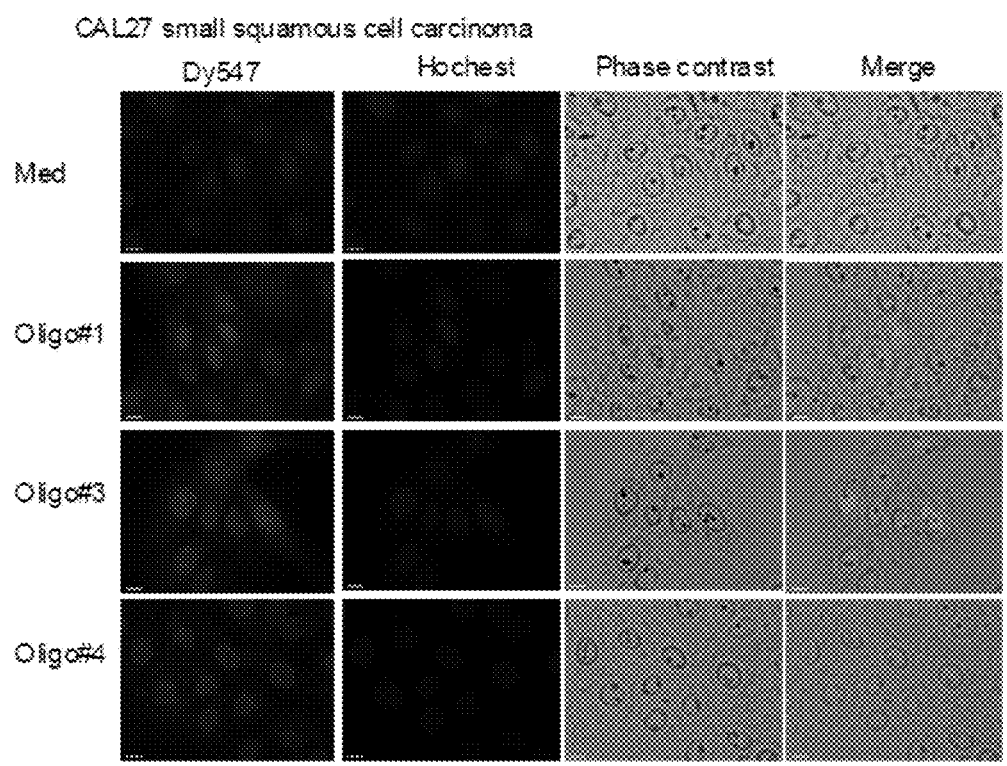
FIG. 5 is an image of CAL27 small squamous cell carcinoma cells transfected by oligonucleotides #1, #3 and #4 as described herein.
Figure 6:
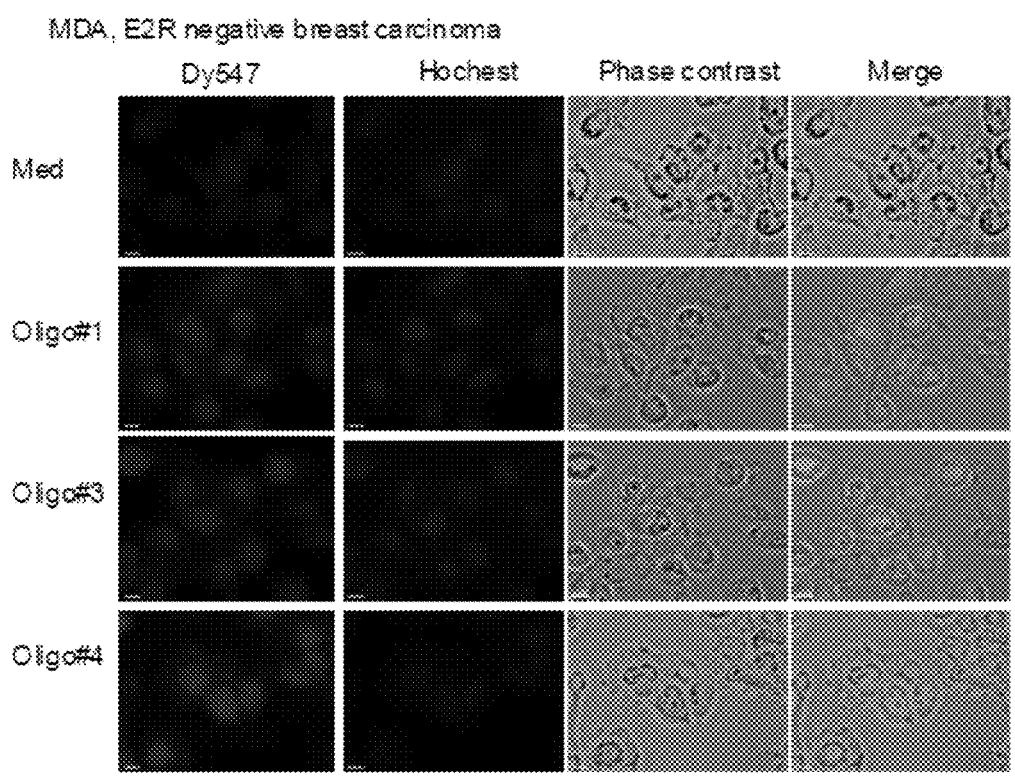
FIG. 6 is an image of MDA, E2R negative breast carcinoma cells transfected by oligonucleotides #1, #3 and #4 as described herein.
Figure 7:
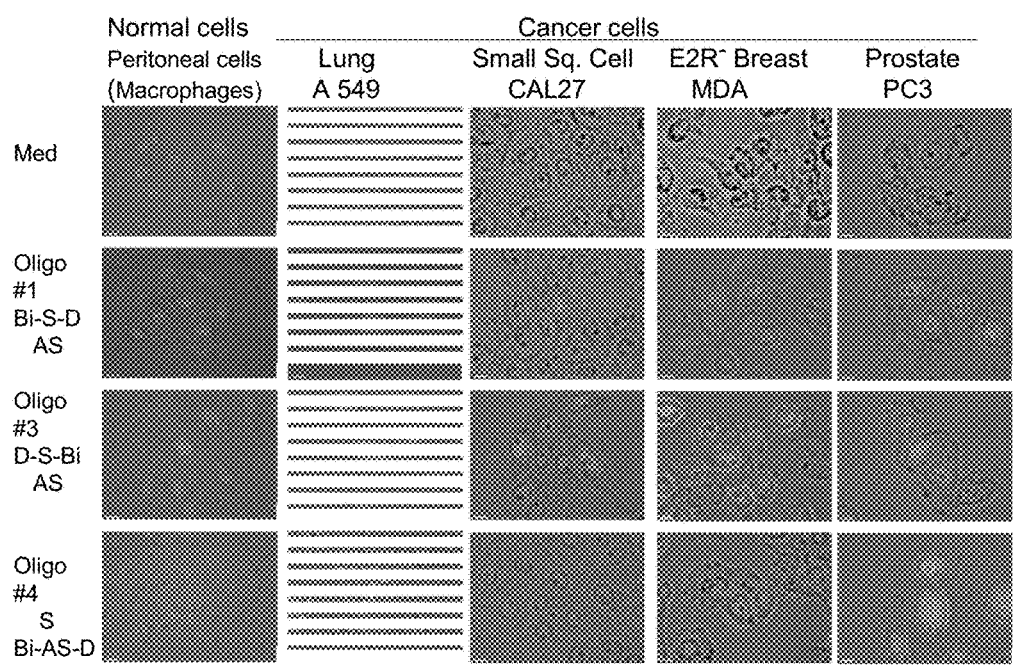
FIG. 7 is an image of A549 lung carcinoma cells, CAL27 small cell carcinoma cells, E2R negative breast carcinoma cells and PC3 prostate cancer cells transfected by biotin conjugated oligonucleotides #1, #3 and #4 as described herein.

In order to deliver the siRNA in vivo we investigated PEI-based delivery as well as the vector free Accell-siRNA transfection in rodent brain. Low molecular weight PEI (Jet-PEI and F25 PEI) relies on non-covalent formation of PEI and RNA molecules, where the RNA is protected and the complex enter the cells via endocytosis. We found severe losses of GFP fluorescence and NeuN immunostaining after single PEI injection in the striatum of Actin-eGFP expressing mice (FIGS. 3A & B)

We tested siRNA transfection in vivo, using the Accell-siRNA system. In order to evaluate the transfection of cells in vivo and distribution of intracerebral injections of the molecules, we used Accell-siRNA where the siRNA molecule were labelled with Fluorescein (FAM) dye. Single injections of 2 ul (0.05 umol/ul) siRNA lead to intense fluorescent signal in the striatum and corpus callosum (cc)/cortex, seen as a column streching from the ventral part of the cortex through the cc to the striatum after 3 days in vivo (FIG. 3C). On-going, we have injected single doses of the pre-designed Accell-siRNA against tau (0.06 nmol in 3 ul), which siRNA showed significant knockdown in primary neuronal cultures, in the hippocampus and cortex of human P301S mutant tau transgenic mice, the areas showing most robust expression and hyperphosphorylation of mutant human tau in the mouse model.

Our data represent an important step forward in investigating the effect of siRNA interference in a clinical relevant model of human Tau-related disease. Moreover, applications in an animal's model of the disease will further shed light on the effect of siRNA interference and its application as a treatment for Tauopathies and related disorders.

Example 6 shRNA Plasmid Construction

The tRNA-valine promoter was constructed by annealing two primers:

```
forward
                                         (SEQ ID NO: 9)
5'-CAGGACTAGTCTTTTAGGTCAAAAAGAAGAAGCTTTGTAACCGTTGG TTTCCGTAGTGTA-3'
and reverse
                                        (SEQ ID NO: 10)
5'-TTCGAACCGGGGACCTTTCGCGTGTTAGGCGAACGTGATAACCACTA

CACTACGGAA ACCAAC-3',
``` extending the primers with PCR, and cloning them into pCR 2.1-TOPO vector using the TOPO TA Cloning Kit (Invitrogen Life Technologies, Carlsbad, Calif.). Head-to-head 21 bp shRNA fragments were PCR amplified using as a template the resulting tRNA-valine promoter in the Topo TA vector, the forward primer above and the reverse primers below. Each shRNA fragment was subsequently cloned into pCR 2.1-TOPO vector. Reverse primers used for generation of tRNA-valine driven shRNA are as follows:

```
Miscellaneous.tvMiss.
                                         (SEQ ID NO: 11)
AAAAAAATGAACTTCCCCGTCAGCTTGCAAGCTTCCAAGCTGACGGGGAA

GTTCATCTTCGAACCGGGGACCTTTCG.
```

-continued

Tau.tvTau:
(SEQ ID NO: 12)
AAAAAAGTGGCCAGGTGGAAGTAAAATCCAAGCTTCGATTTTACTTCCAC

CTGGCCACCTTCG AACCGGGGACCTTTCG.

tvA10:
(SEQ ID NO: 13)
AAAAAAGGTGGCCAGATGGAAGTAAACCAAGCTTCGTTTACTTCCATCTG

GCCACCCTTCGAACCGGGGACCTTTCG.

APP.tvAPP:
(SEQ ID NO: 14)
AAAAAATGAAGTGAAGATGGATGCAGCCAAGCTTCGCTGCATCCATCTTC

ACTTCACTTCGA ACCGGGGACCTTTCG.

tvT10/C11:
(SEQ ID NO: 15)
AAAAAATGAAGTGAATCTGGATGCAGCCAAGCTTCGCTGCATCCAGATTC

ACTTCACTTCGA ACCGGGGACCTTTCG.

Cell Culture and Transfections

Methods for culturing Cos-7 and HeLa cells have been described previously. Plasmids and siRNAs were transiently transfected with Lipofectamine Plus (Invitrogen) in 12-well plates with cells plated at 70-90% confluency. Except where noted a 5:1 ratio of siRNA to expression plasmid was transfected into cells, while for tRNA-valine shRNA experiments, a 10:1 ratio of shRNA plasmid to expression plasmid was used. Transfection efficiency ranges from 50 to 70% under these conditions by visual counting of live fluorescent cells in random fields (data not shown).

Western Blot Analysis

Lysates from Cos-7 cells expressing GFP and tau constructs were harvested 24 h after transfection, while APP and APPsw expressing cell lysates were harvested at 48 h. Lysates from HeLa cells expressing endogenous lamin were harvested at 72 h after transfection of anti-lamin siRNA. Lysates were analyzed by western blot as reported previously. GFP and lamin were detected with anti-GFP mouse monoclonal antibody (1:1000 dilution; Medical and Biological Laboratories, Naka-ku Nagoya, Japan) and anti-lamin goat polyclonal antibody (1:25 dilution; Santa Cruz Biotechnology, Santa Cruz, Calif.) respectively. Additional antibodies used in this study include anti-tau mouse monoclonal antibody at 1:500 dilution (Calbiochem, San Diego, Calif.), 22C11 anti-APP mouse monoclonal antibody at 1:500 dilution (Chemicon International, Temecula, Calif.), and as a loading control, mouse monoclonal antibody to α-tubulin at 1:20 000 dilution (Sigma, St Louis, Mo.). Secondary antibodies were peroxidase-conjugated donkey anti-goat or peroxidase-conjugated donkey anti-mouse (Jackson ImmunoResearch Laboratories, West Grove, Pa.) at 1:15 000 dilution.

Results

An efficient way to create siRNAs against a gene of interest is to produce short RNA duplexes complementary to the target gene in in vitro transcription reactions employing T7 RNA polymerase. However, the priming requirements for T7 polymerase dictate that a G be the priming nucleotide initiating transcription. This limits the nucleotide positions in a target gene to which corresponding in vitro transcribed RNA duplexes can be generated. To overcome this restriction imposed by T7 RNA polymerase, we designed siRNAs that contained a non-complementary G nucleotide at the 5' ends. The resulting siRNA contains 20 complementary nucleotides on the antisense strand with a single 5' mismatch to the target. This incorporation of an initiating G should in principle allow dsRNAs to be generated in vitro against any 20-nucleotide segment of a targeted gene.

To determine whether adding this non-complementary G still produced effective siRNAs, we compared the silencing capability of this novel '+G' configuration to in vitro synthesized siRNA that was perfectly complementary to the target. Suppression of a reporter gene product, GFP and of an endogenous gene product, lamin, may be assessed. Cos-7 cells were co-transfected with a plasmid encoding GFP and siRNAs containing either a perfect match to the GFP mRNA or the single 5' G mismatch. siRNAs containing multiple mismatches were used as negative controls for any non-specific effects of the transfection or siRNA. As assessed by fluorescence microscopy and western blot, the 5' mismatched siRNA displayed silencing efficiency similar to that of the perfectly matched siRNA targeted to the same region of the GFP mRNA.

The ability of these siRNAs to inhibit expression of an endogenous gene product, lamin, may be investigated. HeLa cells were transfected with a negative control siRNA (siMiss) or a siRNA directed against endogenous lamin, and assessed expression 72 h after transfection. Lamin expression was markedly reduced in cells transfected with siLamin+G, but remained robust in cells transfected with siMiss+G. Thus, '+G' siRNA remains an effective trigger of RNA interference.

Discussion

RNAi holds promise as a potential therapy for human diseases. Yet a limitation to successfully developing gene-specific or allele-specific siRNAs is the selection and design of siRNAs with the desired silencing characteristics. Individual siRNAs targeted to different regions of a transcript often display striking differences in efficacy and specificity. Typically, several target sites and designs need to be tested before optimal silencing is achieved. Here we have described a simple method that not only circumvents the time and cost disadvantages of chemically synthesizing siRNA duplexes but also removes the sequence restrictions imposed by in vitro transcription with T7 polymerase.

The insertion of a single G mismatch at the 5' of the siRNA duplex permitted efficient priming by T7 polymerase without compromising the silencing efficacy of the resultant siRNA. Such '+G' siRNAs can rapidly be generated to essentially any point in a targeted gene and tested for efficacy. This approach to siRNA design should facilitate the in vitro generation of effective siRNAs. As demonstrated here for tau and APP, these in vitro transcribed duplexes can then serve as guides for producing shRNA plasmids that retain silencing capability and allele specificity. This approach represents an improved, stepwise method for optimized silencing of essentially any gene of interest.

Preferential entry of the guide, or antisense, strand into RISC can be achieved by introducing 5' mismatches in the antisense strand while maintaining perfect base pairing at the 5' terminus of the sense strand. This maximizes entry of the antisense strand into the RISC complex while also reducing potential off-target inhibition by the sense strand. The '+G' approach to siRNA design is perfectly suited to engineering dsRNAs based on this principle that should display preferred RISC entry of the guide strand.

In certain embodiments, for tau and APP, central placement of mismatches results in optimal allele-specific silencing of mutant alleles. With the APPsw double mutation, for example, placing the two mismatches immediately across from the predicted RISC cleavage site resulted in highly specific allele discrimination. Together with recent findings by others, these results demonstrate the importance of central placement of mutations for successful allele-specific silencing.

For tau, however, siRNAs with centrally placed mismatches still retained some activity against the wild type allele. This suggests that both the position of the mismatch along the guide strand and the chemical nature of the mismatch are important for determining whether RISC associated nucleases will cleave a given mRNA. This is consistent with results suggesting that disruption of the predicted structure between mRNA and the RISC-associated guide strand will prevent cleavage. Systematic testing of RISC-mediated cleavage in vitro strongly suggests that cleavage occurs across from the central nucleotides of the guide strand, most likely 9-11 nucleotides from the 5' end. While perfect base pairing is optimal, some mismatches are less disruptive and still permit partial cleavage activity. For example, in RNAi studies targeting a single nucleotide change in the polyglutamine disease gene MJD1, a G-G clash between the antisense strand of the siRNA and the target mRNA resulted in a complete inability to silence the wild type allele while the mutant allele was strongly suppressed. In contrast, even with the tau (V337M) mutation optimally placed centrally in the siRNA, we continued to observe some silencing of wild type tau. This suggests that the less disruptive G-U clash in the case of the tau mutation does not allow for complete allelic discrimination by siRNA. In such cases additional mismatches may need to be incorporated into the siRNA.

The RNAi reagents developed here constitute an experimental and potential therapeutic advance for AD and related dementias. Although abnormal deposition of tau and the APP cleavage product Aβ are central to AD pathogenesis, the precise roles of these proteins in the brain remain to be elucidated. These siRNA reagents, which can be used to selectively silence expression of mutant or wild type tau and APP, should facilitate loss of function experiments aimed at identifying the neuronal functions of these proteins.

For potential therapeutic applications of siRNA, we have established expression vectors that silence mutant or wild type forms of tau and APP. For individuals with dominantly inherited AD or tauopathy, selective removal of the mutant protein might ameloriate or even prevent disease. The demonstration of specific silencing of mutant alleles extends the potential utility of the approach to genes with important or essential functions. For APP we achieved specific silencing of either the widely studied Swedish double mutant or wild type APP. Reagents that suppress APPsw should be useful in testing RNAi therapy in mouse models of AD, and reduction of wild type APP may also have therapeutic potential for the common, sporadic form of AD. Based on the amyloid cascade hypothesis of AD, the most selective intervention would be a reagent that suppresses APP protein production with minimal effects on unintended target. Aβ production requires cleavage of APP by two proteases, the β site APP-cleaving enzyme BACE and the γ-secretase complex, which contains presenilin. Thus, additional gene targets in AD include BACE and, for most familial AD, dominantly acting presenilin mutations.

REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

EQUIVALENTS

The present invention provides, among other things, biotinylated compositions comprising siRNA. While specific embodiments of the subject invention have been discussed, the above specification is illustrative and not restrictive. Many variations of the invention will become apparent to those skilled in the art upon review of this specification.

I claim:

1. A composition comprising a biotin moiety and a siRNA moiety, wherein the siRNA moiety comprises a nucleotide of SEQ ID NO: 2 or a nucleic acid that has at least 95% sequence homology with SEQ ID NO: 2.

2. The composition of claim 1, wherein the composition further comprises a linker between the siRNA and the biotin.

3. The composition of claim 1, wherein the composition does not comprise an antibody, an antigen, avidin, or streptavidin.

4. The composition of claim 1, wherein the composition further comprises a diagnostic agent.

5. The composition of claim 4, wherein the diagnostic agent is selected from the group consisting of a fluorophore, a chromophore, a chemoluminescing agent, a radionuclide, an unpair spin atom, a free radical, and a contrast agent.

6. The composition of claim 1, wherein the composition is able to transfect cells in vivo.

7. The composition of claim 1, wherein the composition partially, substantially, or completely deletes, silences, inactivates, interferes with, or down-regulates a gene that encodes selenoprotein P.

8. The composition of claim 1, wherein the siRNA moiety comprises a guanosine at the 5'-end.

9. The composition of claim 1, wherein the sense or the antisense strand of the siRNA moiety is equal to or less than 30 nucleotides in length.

10. A pharmaceutically acceptable formulation, wherein the pharmaceutically acceptable formulation comprises a therapeutically-effective amount of a composition of claim 1 and a pharmaceutically acceptable carrier or diluent.

11. A method generating an image of a subject, comprising the steps of:
   administering to a subject in need of imaging a detectable amount of a composition of claim 4, and
   generating an image.

12. The method of claim 11, wherein said subject is a human.

* * * * *